US00PP08752P

United States Patent [19]

Hanes

[11] Patent Number: Plant 8,752

[45] Date of Patent: May 24, 1994

[54] GERANIUM NAMED AMERICANA RED

[75] Inventor: Mitchell Hanes, Morgan Hill, Calif.

[73] Assignee: Goldsmith Seeds, Inc., Gilroy, Calif.

[21] Appl. No.: 50,530

[22] Filed: Apr. 20, 1993

[51] Int. Cl.[5] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by the semi-double red flowers. The plant itself is strong and basal branching, growing to a height of 16–20 cm. as a 6 inch potted plant.

1 Drawing Sheet

BACKGROUND OF THE NEW PLANT

The present invention comprises a new and distinct tetraploid cultivar of geranium, botanically known as *Pelargonium hortorum* Bailey. The new cultivar is propagated from a seedling resulting from the cross of two tetraploid, unreleased, proprietary, inbred lines: a red color single flower seed parent derived from one of our breeding lines known as 800-1 and a pollen parent known as 718-3, that is a red colored semi-double flowered plant.

This new plant is a product of a planned breeding program intended to create new geranium cultivars with red colored semi-double flowers, green foliage, with vigorous growth and superior cutting productivity.

The new cultivar was created in 1988 in Gilroy, Calif. and has been repeatedly asexually reproduced by cuttings in Gilroy, Calif. and Guatemala over a four year period. It has also been trialed at Okemos, Mich. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed description set forth the distinctive characteristics of this new geranium. The data which defines these characteristics was collected from asexual reproductions carried out in Gilroy, Calif. The plant history was taken on 20 week old plants, blossomed under natural light in a greenhouse. Color readings were taken in the greenhouse on Mar. 14, 1993 under ambient light. Color references are primarily to the R.H.S. Colour Chart of The Royal Horticultural Society of London.

THE PLANT

Classification:

*Botanical.*—*Pelargonium hortorum* Bailey.

*Commercial.*—Zonal geranium.

Form: Basal branching. With age, the diameter of the plant increases.

Height: 16 to 20 cm. as a 6 inch potted plant, excluding blooms.

Growth: Well controlled when grown in pots, very strong when planated in garden.

Internode: Approximately 1–1.5 cm. in length.

Strength: Very good cutting producer for propagation, and the plant performs very well after shipping as a rooted or unrooted cutting. Cuttings are fast to root.

Foliage: Abundant quantity.

*Leaves.*—Normal.

*Size.*—Diameter about 8 cm.

*Shape.*—Rounded with occasional upfolding between veins.

*Margin.*—Irregularly crenate.

*Texture.*—Leathery and pubescent on both surfaces, especially along veins.

*Ribs and veins.*—Distinctly palmate, 3.6 to 5.0 cm. long.

*Color.*—Upper side: Green RHS 143A-B with darker green zonation RHS 143A extending inward 2.5 cm. from the leaves edge. Under side: Lighter green color. Ribs and veins not prominently different from the upper surface. This differentiates the leaf color from that of Eclipse Red, U.S. Plant Pat. No. 7,959, which has leaf color, RHS 137B.

*Petioles.*—About 4.2 to 8.5 cm. in length.

THE BUD

Size:

*Diameter.*—About 8 mm.

*Length.*—About 2.0 to 2.9 cm. at the time of bud opening.

Shape: Pointed ovoid.

Color: Of petals when sepals first divide, RHS 53-D.

Sepals: Five in number, flat behind petals, pointed linear lanceolate, RHS 144-C in an open flower.

THE FLOWER

Blooming habit: Continuous throughout the year, when grown in a frost free environment.

Size: Approximately 5.0 cm. in diameter, 1.7 cm. deep, irregularly radially symmetrical.

Form: Cup-shaped when bloom first opens, later flattening to shallow cup shape with maturity.

Petals: Five imbricate outer petals, 2.5–2.9 cm. wide and approximately 2.6 cm. long. Six to eight inner smaller petaloids of varying shape. Both the outer petals and inner petaloids are red, RHS 44-B. Color changing little with age. Under side of petals lighter in color and showing white at the base. Petals and petaloids are soft and satiny.

Peidicel: Approximately 3.7 cm. in length.

Persistence: Nonshattering flower. Removal of spent flowers grooms the plant but is not necessary to maintain continuous flowering.

INFLORESCENCE

Type: An umbel composed of approximately 35 flowers, erect or laterally ascending, with a maximum diameter of about 12 cm. On a 12 week old plant in a 6" pot typically there will be 2–3 umbels.

Peduncle: Approximately 11–14 cm. in length, usually 12 cm. Green in color with slight reddish pigmentation on the side exposed to the sun.

REPRODUCTIVE ORGANS

Stamens:

*Anthers.*—Five to eight positioned below the mature stigma, dull red prior to anthesis.

*Filaments.*—White near base and mid-length, graduating to orange-red near the anther.

*Pollen.*—Orange in color.

Pistil:

*Number.*—One.

*Length.*—Approximately 5 mm.

*Stigma.*—Five linear lobes of near equal length, curling back toward the ovary, purplish-red in color.

Style:

*Length.*—About 3 mm.

*Color.*—Orange.

Ovaries: At anthesis, densely pubescent with white hairs, oblong. Green drying to a light brown at maturity.

Fruit: Partially fertile.

I claim:

1. A new and distinct geranium cultivar substantially as herein shown and described, characterized by its red colored, semi-double flowers on large umbels, green foliage without a distinct zonation; the plant being fast rooting and having a vigorous basal branching growth habit.

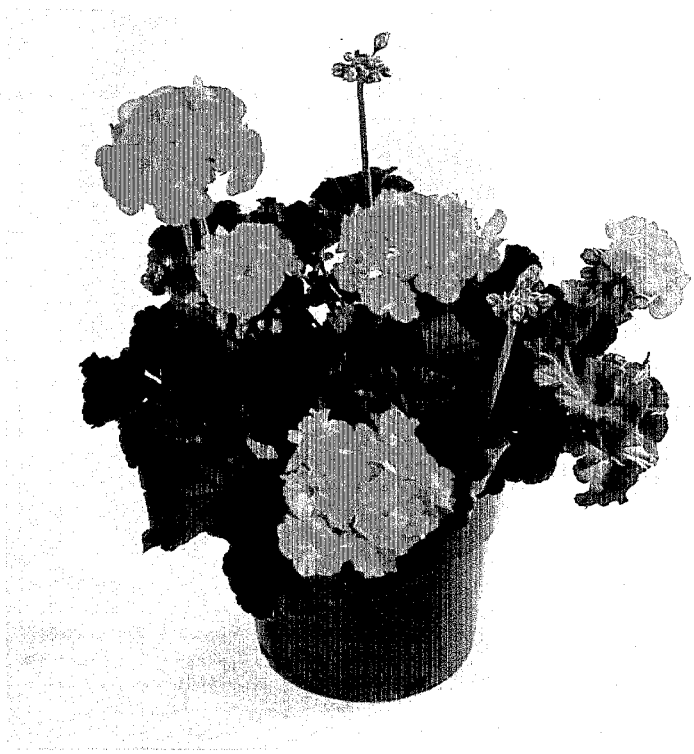

* * * * *